United States Patent [19]

Abernathy et al.

[11] 4,306,105

[45] Dec. 15, 1981

[54] PROCESS FOR THE PRODUCTION OF POLYISOBUTENES

[75] Inventors: Marshall W. Abernathy; James M. Watson, both of Big Spring, Tex.; Georges E. M. J. De Clippeleir; Raymond M. Cahen, both of Brussels, Belgium

[73] Assignee: Cosden Technology, Inc., Dallas, Tex.

[21] Appl. No.: 189,429

[22] Filed: Sep. 22, 1980

[51] Int. Cl.$^3$ ............................................... C07C 2/02
[52] U.S. Cl. ................................................... 585/533
[58] Field of Search ............................. 585/533, 532

[56] References Cited

U.S. PATENT DOCUMENTS 3,600,129 8/1971 Vesely et al. ...................... 585/533
3,607,959 9/1971 Estes et al. ......................... 585/533

*Primary Examiner*—Curtis R. Davis

[57] ABSTRACT

A process for selectively producing liquid polyisobutene contacting a feed stream containing mixed butenes with a dry chlorinated alumina catalyst at a temperature of from about −15° to about 50° C. wherein the chlorinated alumina contains from about 2 to 20% by weight of chlorine and the alumina has a purity of at least 99% and a surface area greater than 150 m$^2$/g with at least 10% of the pores having a mean diameter larger than 200Å and recovering polyisobutenes having a molecular weight between about 280 and 4000.

13 Claims, No Drawings

PROCESS FOR THE PRODUCTION OF POLYISOBUTENES

BACKGROUND OF THE INVENTION

The present invention relates to a process for the production of polyisobutenes from a gas feed stream comprising monomers of mixed butenes as well as saturated $C_4$ hydrocarbons and optionally some lower and higher hydrocarbons.

A widely used known process for polymerizing low molecular weight olefins consists in passing the olefins through a catalyst suspended in a liquid slurry. The resulting polymer contains significant amounts of catalyst and must, therefore, be subsequently treated by costly and time-consuming techniques to remove the catalytic material which it contains.

To obviate this drawback, it has been suggested to carry out the polymerization of olefinic feeds in the presence of a solid catalyst by using the fluidized bed technique as described in U.S. Pat. No. 2,446,619. However, this process has not proven itself effective to form materials beyond dimers.

U.S. Pat. No. 3,017,400 teaches the polymerization of olefins by passing the feed through a catalyst material, such as aluminum chloride and ferric chloride. However, these catalysts are not very active and they have a relatively short life. In a similar fashion, U.S. Pat. No. 3,558,737 discloses that catalysts useful for hydrocarbon conversions, for example, isomerization, alkylation, polymerization, can be prepared by activating alumina, either alone or in admixture with a chlorinated organic compound or with an organic compound in the presence of chlorine. These catalysts are suitable in a plurality of hydrocarbon processes, but when employed for polymerizing olefins, they yield only lower molecular weight polymers. Moreover, when used for polymerizing feeds comprising mixed butenes, these catalysts give polymers containing large amounts of poly-n-butenes and small amounts of polyisobutenes. These catalysts are also only active for relatively short periods of life.

There is, therefore, a need for a process which can be undertaken for long periods of time and which allows the selective polymerization of isobutene from a gas feed stream containing monomers of mixed butenes. It is also highly desirable to obtain liquid polyisobutenes having a molecular weight of at least 280. The latter are valuable products for many uses, for example, as additives in lubricating oils, insulating oils and the like due to their increased viscosity when compared with the corresponding poly-n-butenes having the same molecular weight.

SUMMARY OF THE INVENTION

It is, therefore, an object of the present invention to provide a method of polymerizing butenes to produce polyisobutenes essentially free of catalyst contaminants and suitable for use directly without purification.

Another object of the present invention is to provide a method of selectively polymerizing isobutene contained in a feed stream of mixed butenes.

A further object of the present invention is to provide a method of producing polyisobutenes having a molecular weight higher than 280 and controllable with the change of the reaction conditions.

It is also an object of the present invention to provide a method of polymerizing butenes using economic amounts of a highly active and selective catalyst.

Yet another object of this invention is to provide a process for the selective polymerization of isobutene in the presence of a catalyst which exhibits long term activity and which is effective for long periods of time without the necessity of regeneration.

The present invention contemplates a process for selectively producing liquid polyisobutenes comprising contacting a feed stream containing mixed butenes with a dry chlorinated alumina catalyst at a temperature of from about $-15°$ to about $50°$ C., wherein the chlorinated alumina contains from about 2 to 20% by weight of chlorine and the alumina has a purity of at least 99% and a surface area greater that about 150 $m^2/g$ with at least 10% of the pores having a mean diameter larger than 200 Å, and recovering polyisobutenes having a molecular weight between about 280 and 4000.

The process is applicable to the selective polymerization of isobutene contained in a feed consisting of mixed butenes, i.e. mixtures of 1-butene, trans- and cis-2-butenes and isobutene. The feed may also contain butanes and optionally some lower and higher hydrocarbons. In practical polymerization, the isobutene is usually present in an amount of at least about 8% and more generally, in an amount which may vary between about 10 and 90 weight percent. Refinery liquified $C_4$ fractions, such as for example, fractions resulting from naphtha steam cracking or catalytic cracking (after removal of butadienes and acetylenic hydrocarbons) are particularly valuable feed stocks. Typical compositions of these feeds are the following (% by weight):

|  | Naphtha Steam Cracking | Catalytic Cracking |
| --- | --- | --- |
| n-butane | 0.84 | 23.89 |
| isobutane | 1.57 | 29.42 |
| isobutene | 47.84 | 12.79 |
| 1-butene | 32.27 | 13.59 |
| cis-2-butene | 7.15 | 7.89 |
| trans-2-butene | 10.33 | 12.42 |

The chlorinated alumina catalyst comprises substantially pure alumina and chlorine. The term "substantially pure alumina" means alumina wherein the $SiO_2$ content does not exceed about 0.6 wt % and the $Na_2O$ content is lower than about 0.6 wt %, the total content of these impurities as well as Fe and S compounds as impurities being lower that 1 wt.%. It has been unexpectedly found that some impurities and more particularly, $Fe_2O_3$, and S have a detrimental effect on the formation of polyisobutenes having the desired molecular weight and lead to polymers containing essentially dimers and trimers. Accordingly, the chlorinated alumina catalyst is prepared from alumina having a purity of at least 99%. Aluminas having a purity of 99.5% and higher are particularly suitable.

The preferred chlorine atoms concentration of the catalyst depends upon many factors, such as for example, the surface area of the alumina. Moreover, in many cases, the greater the amount of chlorine, the higher is the activity of the catalyst. However, it has been found that highly active catalysts are generally less selective. For these reasons, the chlorine content is preferably within the range of 2 to 20 wt.%, more particularly between about 4 and about 15 wt.%. It is generally preferable and desirable to use a catalyst containing at least about 5 chlorine atoms per 100 square Å in order to selectively and efficiently produce polyisobutenes from monomers of mixed butenes.

Any of the forms of alumina customarily employed in catalysts may be used, but a particularly suitable form is one containing a major proportion of eta or gamma alumina. It has been found that the catalyst material is highly active and selective when the surface area of the alumina before chlorination is at least about 150 m$^2$/g. The process of this invention is advantageously applied when the alumina has a surface area greater than about 200 m$^2$/g, and which may reach about 350 m$^2$/g.

Chlorinated alumina prepared from alumina wherein at least 10% of the pores have a diameter larger than 200 A are preferably used in the present process. More particularly, polyisobutenes with a low content of dimers and trimers are produced when at least 20% of the pores have a diameter larger than 200 A. Alumina wherein the diameter of the pores exceeds about 150,000–200,000 A are less suitable as they yield polyisobutenes having excessively high molecular weights.

It has been found that high yields of polyisobutenes are obtained when the alumina has a total pore volume of at least about 0.25 ml/g before chlorination. However, catalyst materials exhibiting excessively large total pore volumes also possess a low strength. For these reasons, the total pore volume of the alumina before chlorination is preferably within the range of about 0.6 to about 1.2 ml/g.

Chlorinated alumina meeting the above conditions can be produced in any shape known in the art, such as for example, in pellet, extrudate, granular or bead form. The shaped alumina can then be used in a fixed bed or moving bed through which the feed is passed. The temperature within the reactor is maintained between about $-15°$ C. and about 50° C. The reactor may be provided with any conventional means to control the temperature of the exothermic reaction. The temperature depends upon the particular catalyst used, the composition of the feed and also upon the desired molecular weight for the polyisobutene (as the molecular weight decreases when the temperature is increased). In a preferred embodiment, the reaction temperature is maintained between about 0° C. and about 50° C.

The pressure within the reactor is normally such that the feed to and within the reactor is maintained in the liquid phase and/or in mixed liquid-vapor phase. For the ranges of feed composition contemplated by the present invention, this will normally correspond to a gauge pressure of at least 0.5 kg/cm$^2$. The use of pressures higher than 50 kg/cm$^2$ does not produce any appreciable improvement in yield. In the preferred embodiment, the pressure will not exceed about 10 kg/cm$^2$.

The liquid hourly space velocity (or LHSV) is the volume of liquid feed per hour per volume of catalyst. The LHSV depends on many factors, such as composition of the charge, type of catalyst material, reaction temperature and desired molecular weight of the polymer. A low LHSV gives a correspondingly low molecular weight. A LHSV within the range of about 0.5 to 5 is suitable for the selective polymerization of isobutenes according to this invention. Particularly, suitable polymers have been obtained in the presence of chlorinated alumina at LHSV between about 0.75 and 2.

The process of the present invention affords wide versatility in the control of the molecular weight of the produced polyisobutenes. By appropriate selection of the reaction conditions, isobutene is selectively polymerized to clear and more uniform products consisting of narrow range molecular weight polyisobutenes. For instance, low hourly space velocities and/or high temperatures within the ranges hereinabove specified bring about the formation of polyisobutenes having a molecular weight of about 280 to about 400 (number average molecular weight). Higher hourly space velocities and/or lower reaction temperatures lead to the production of higher molecular weight polyisobutenes. However, for practical reasons, the working conditions are selected so that the molecular weight does not exceed about 4000. Polyisobutenes having a molecular weight greater than 4000 are generally less useful.

The present process is a very specific process for the selective polymerization of isobutene contained in a liquid gas feed comprising other butenes, with production of polyisobutenes $(C_4H_8)_n$ where n usually lies between 5 and about 70. While the reasons for the effectiveness of this process in producing these polyisobutenes are not known, it has been found that the chlorinated alumina used as catalyst material in this process must fulfill the above-given conditions with respect to the chlorine content of the catalyst material, the purity of the alumina and the pore sizes. It has also been discovered that such a catalyst is not only highly selective, but also exhibits a desirable long term activity.

In addition to these advantages, it has also been discovered that catalyst deactivation and consequent reduction of activity and selectivity are low with the process of the present invention. Moreover, the catalyst material is easily regenerated by a usual burnoff procedure and then by rechlorination. The regenerated catalyst material is as active and selective as a fresh catalyst. Preferably, the moisture content of the feed should be reduced as much as possible by any conventional drying technique, for instance, by passing the feed through a molecular sieve.

DETAILED DESCRIPTION OF PREFERRED EMBODIMENTS

In order to more fully illustrate the features of this invention, the following non-limiting examples are presented.

In each run, the reaction product is outgassed at about 120° C. and at atmospheric pressure and is then distilled under vacuum to yield an upper "light" fraction (boiling below 210° C. when measured at atmospheric pressure and consisting mainly in dimers and trimers) and a "heavy" bottom fraction (boiling above about 210° C.). This heavy fraction is the desired fraction. Thus, the selectivity or weight ratio of heavy fraction to light fraction (or H/L ratio) should be as high as possible. The H/L ratio varies with the molecular weight of the heavy fraction. The following minimum H/L ratios are required for the corresponding heavy products:

| Molecular Weight of Heavy Product | Minimum H/L Ratio |
| --- | --- |
| 280–400 | 1.7 |
| 400–600 | 3.0 |
| 600–700 | 4.0 |
| 700–800 | 5.0 |
| 800–1000 | 6.0 |
| 1000–1400 | 8.0 |
| 1400–2000 | 10.0 |

-continued

| Molecular Weight of Heavy Product | Minimum H/L Ratio |
|---|---|
| 2000–2200 | 13.0 |
| 2200–3300 | 17.0 |
| 3300–3500 | 19.0 |

EXAMPLE 1

A feed containing:

| isobutane | 27–31 wt. % |
|---|---|
| n-butane | 7.0–9.5 wt. % |
| 1-butene | 16–19 wt. % |
| isobutene | 22–24 wt. % |
| cis-2-butene | 5–10 wt. % |
| trans-2-butene | 14–16 wt. % | was passed through a fixed bed of chlorinated alumina prepared from an alumina having a surface area of 283 m$^2$/g and a total pore volume of 0.79 ml/g. The volume of pores due to pores with a diameter higher than 200 Å was 0.35 ml/g (44.3% of the total pore volume). The alumina had a purity greater than 99.8% and it contained 0.12% SiO$_2$, 0.014% Na$_2$O, 0.007% Fe$_2$O$_3$ and 0.0075 % S (% by weight). The chlorine content of the chlorinated alumina was 8.0% with 4.8 chlorine atoms per 100 square Å.

The liquid hourly space velocity (LHSV) of the feed was 1 and the pressure in the reactor was 6 kg/cm$^2$.

The following results were obtained:

| Total Elapsed Time (Hours) | Temp. (°C.) | Light Fraction: % wt. on Olefins | Heavy Fraction % wt. on olefins | Mol. wt. | H/L weight ratio |
|---|---|---|---|---|---|
| 773 to 941 | 0–3 | 1.1–1.4 | 22–24 | 3300 | 20 |
| 941 to 1084 | 17–19 | 3.4–4.1 | 25–28 | 965 | 7 |
| 1084 to 1229 | 27–29 | 6.3–6.9 | 25–27 | 595 | 4 |
| 1229 to 1301 | 39–41 | 11–12 | 24–25 | 355 | 2 |

The catalyst was then regenerated (by a conventional burnoff procedure followed by re-chlorination). The regenerated catalyst had the same initial activity as the fresh catalyst. The results obtained during an additional time of about 1500 hours were essentially the same as the results obtained with the fresh catalyst.

By way of comparison, the following experiments were carried out:

COMPARATIVE EXPERIMENT A

A fluoridated alumina (11.1% fluorine) having the same characteristics as the above catalyst material was used at a temperature of 0° C., the other conditions being the same as in Example 1.

The mean molecular weight of the heavy fraction was 870 and the heavy fraction to light fraction ratio (H/L) was only 0.7.

COMPARATIVE EXPERIMENT B

A brominated alumina (17% bromine) having the same characteristics as the above chlorinated alumina was used at 28°–30° C. and all other working conditions were the same as in Example 1.

The mean molecular weight of the heavy fraction was 802 (mean of 256 on stream hours) and the H/L ratio was 4.6.

COMPARATIVE EXPERIMENT C

The same experiment as in Example 1 was carried out, but with the use of a chlorinated alumina prepared from an alumina containing 1.7 wt.% SiO$_2$, 1.4 wt.% Na$_2$O, 0.05 wt.% Fe$_2$O$_3$, 0.03% S. The results obtained after 168 hours were:

| Light fraction: wt. % on olefins | 9.8 |
|---|---|
| Heavy fraction: wt. % on olefins | 22.5 |
| molecular weight | 885 |

This comparative experiment shows that the impurities contained in the catalyst material lead to the formation of a more significant light fraction: the H/L ratio was only 2.3.

EXAMPLE 2

The same feed as in Example 1 was passed through a chlorinated alumina having the following characteristics:

alumina:
total pore volume: 0.93 ml/g
volume of pores with diameter larger that 200 A: 0.52ml/g (55.9% of total pore volume)
surface area: 150 m$^2$/g
purity: greater than 99.8% Al$_2$O$_3$ with 0.12% SiO$_2$, 0.014% Na$_2$O, 0.007% Fe$_2$O$_3$ and 0.007% S
chlorine content: 3.25%

The operating conditions were:

| temperature | 48.5° C. |
|---|---|
| LHSV | 4 |
| pressure | 20 kg/cm$^2$ |

The results were the following:

| light fraction | 8.49 | wt. % on olefins |
|---|---|---|
| heavy fraction | 21.0 | wt. % on olefins |
| molecular weight of the heavy fraction | 384 | |
| H/L ratio | 2.5 | |

EXAMPLE 3

The same feed as in Example 1 was passed through a chlorinated alumina having the following characteristics:

alumina:
total pore volume: 0.53 ml/g
volume of pores with diameter larger than 200A : 0.12 ml/g (22.6% of total pore volume)
surface area : 228 m$^2$/g
purity : > 99.5% Al$_2$O$_3$, 0.02% SiO$_2$, 0.0004% Na$_2$O, 0.015% Fe$_2$O$_3$ and 0.007% S
chlorine content : 7.9%

The operating conditions were:

| temperature | 40° C. |
|---|---|
| LHSV | 1.0 |
| pressure | 6 kg/cm$^2$ |

The heavy fraction had a molecular weight of 345 and was obtained with a yield of 27.4% wt. based on the olefins content of the feed. The H/L ratio was 1.9.

EXAMPLE 4

The same feed as in Example 1 was passed through a chlorinated alumina having the following characteristics:

alumina:
total pore volume : 0.45 ml/g
volume of pores with diameter larger than 200A : 0.06 ml/g (13.3%)
surface area : 294 m$^2$/g
purity : 99% Al$_2$O$_3$ 0.6% Na$_2$O, 0.015% Fe$_2$O$_3$ and 0.09% S.
chlorine content : 9.7%.

Different runs were carried out under a pressure of 6 kg/cm$^2$ and with a LHSV of 1, at different temperatures. The results are given in the following table.

| Temperature (°C.) | 3-5 | 28-30 | 39-40 | 44-46 |
| --- | --- | --- | --- | --- |
| Heavy fraction | | | | |
| molecular weight | 1760 | 760 | 453 | 368 |
| wt. % on olefins | 25.1 | 26.6 | 23.8 | 22.0 |
| H/L ratio | 15.7 | 6.8 | 3.6 | 2.6 |

EXAMPLE 5

A feed having the following composition:

| isobutane | 2-3 wt. % |
| --- | --- |
| n-butane | 9-10 |
| 1-butene | 27-29 |
| isobutene | 49-51 |
| cis-2-butene | 2-3 |
| trans-2-butene | 7-8 | was passed through the catalyst described in Example 1. The operating conditions were:

| temperature | 40° C. |
| --- | --- |
| pressure | 6.0 kg/cm$^2$ |
| LHSV | 0.5 and 1 |

The results were the following:

| LHSV | 0.5 | 1.0 |
| --- | --- | --- |
| Heavy fraction | | |
| molecular weight | 535 | 548 |
| wt. % on olefins | 40.5 | 33.9 |
| H/L ratio | 3.3 | 3.3 |

What is claimed is:

1. Process for selectively producing liquid polyisobutenes comprising contacting a feed stream containing mixed butenes with a dry chlorinated alumina catalyst at a temperature of from about $-15°$ C. to about 50° C., wherein said chlorinated alumina contains from about 2 to about 20% by weight of chlorine and the alumina has a purity of at least 99% and a surface area greater than about 150 m$^2$/g with at least 10% of the pores having a diameter larger than 200 Å and recovering polyisobutenes having a molecular weight between about 280 and 4000.

2. The process of claim 1 wherein said alumina has a SiO$_2$+Na$_2$O+Fe$_2$O$_3$ content lower than 1 wt. %.

3. The process of claim 1 wherein said chlorinated alumina contains from about 4 to about 15% by weight of chlorine.

4. The process of claim 1 wherein said alumina has a surface area from about 150 m$^2$/g to about 350 m$^2$/g before chlorination.

5. The process of claim 4 wherein said alumina has a surface area from about 200 m$^2$/g to about 350 m$^2$/g before chlorination.

6. The process of claim 1 wherein at least 20% of the pores of the alumina have a diameter between about 200 Å and 200,000 Å.

7. The process of claim 1 wherein said alumina has a total pore volume of at least about 0.25 ml/g before chlorination.

8. The process of claim 7 wherein said chlorinated alumina has a total pore volume comprised between about 0.6 and 1.2 ml/g.

9. The process of claim 1 wherein the contacting step is conducted under a gauge pressure between 0.5 and 50 kg/cm$^2$.

10. The process of claim 9 wherein said pressure is between 0.05 and about 10 kg/cm$^2$.

11. The process of claim 1 wherein the contacting step is carried out at a liquid hourly space velocity within the range of about 0.5 and 5.

12. The process of claim 11 wherein said velocity is between about 0.75 and 2.

13. The process of claim 1 wherein the temperature is between about 0° C. and 50° C.

* * * * *